United States Patent [19]

Larson

[11] 4,362,649

[45] Dec. 7, 1982

[54] CATALYST COMPOSITION FOR BODY TEMPERATURE OF LIQUID POLYTHIOPOLYMERCAPTAN POLYMERS FOR MAKING ELASTOMERIC DENTAL IMPRESSIONS

[75] Inventor: Melvin L. Larson, Ann Arbor, Mich.

[73] Assignee: Sybron Corporation, Rochester, N.Y.

[21] Appl. No.: 247,231

[22] Filed: Mar. 25, 1981

[51] Int. Cl.$^3$ .................... B01J 31/02; B01J 31/26
[52] U.S. Cl. .................... 252/430; 528/374; 523/109; 523/200
[58] Field of Search ............ 260/37 R; 252/430; 528/374; 523/109, 200

[56] References Cited

U.S. PATENT DOCUMENTS

| | | | |
|---|---|---|---|
| 3,362,927 | 1/1968 | Lochridge | 260/37 R |
| 3,637,612 | 1/1972 | Bertozzi | 528/374 |
| 3,923,754 | 12/1975 | Pellico | 260/37 R |
| 4,082,693 | 4/1978 | Kessler et al. | 528/374 |

*Primary Examiner*—Charles F. Warren
*Assistant Examiner*—Raymond Covington
*Attorney, Agent, or Firm*—Theodore B. Roessel; Owen D. Marjama

[57] ABSTRACT

An elastomeric dental impression catalyst composition for mouth temperature curing of liquid polythiopolymercaptan polymers comprised of propionic acid-treated, submicron zinc oxide and purified benzothiazyl disulfide (2,2$^1$-dithiobis-(benzothiazole)) is disclosed. The composition contains at least 20 parts by weight of the propionic acid-treated, submicron zinc oxide and less than 20 parts by weight of substantially pure benzothiazyl disulfide, with the amount of each of the zinc oxide and the benzothiazyl disulfide being based upon 100 parts by weight of the polymer. The final cured composition is also disclosed.

5 Claims, No Drawings

CATALYST COMPOSITION FOR BODY TEMPERATURE OF LIQUID POLYTHIOPOLYMERCAPTAN POLYMERS FOR MAKING ELASTOMERIC DENTAL IMPRESSIONS

PRIOR ART

The present invention relates in general to a dental composition, and more specifically to a catalyst composition suitable for use in curing a base paste composition which is used to form a dental impression.

Although substantial patent literature exists on the room temperature cure of polythiopolymercaptan polymers, primarily for sealant, coating and adhesive applications, very little prior art relates to the fast, suitable cure for a dental impression material.

Dental requirements are that the system cure inside the human mouth within about ten minutes, give certain properties of compression set, exhibit resistance to stress and provide dimensional stability. Only the zinc oxide containing systems giving relatively rapid cure will be discussed as relevant to the novelty and superiority of the present invention.

It has long been recognized that zinc oxide by itself will promote a slow room temperature cure of thiol group containing polysulfide polymers. The problem has been to accelerate the cure sufficiently to obtain a catalyst system sufficiently fast and appropriate for dental impression use. One such teaching is disclosed in U.S. Pat. No. 3,362,927 (Lockridge, 1968) in which dimethyl sulfoxide is added to a polythiopolymercaptan polymer containing base and zinc oxide is contained in the catalyst. Dimethyl sulfoxide, however, is known to have independent and undesirable oxidizing properties towards thiols, producing a dimethyl sulfide by-product. Another prior art teaching is directed to the activation of zinc oxide by aqueous acetic acid, as disclosed in the U.S. Pat. No. 3,637,612 (Bertozzi, 1972). The presence of water, however, is undesirable with respect to the shrinkage of the resultant elastomer.

Another prior art teaching which is relevant to the present invention is U.S. Pat. No. 3,923,754 (Pellico, 1974) which discloses the use of at least 20 parts by weight of benzothiazyl disulfide, based upon 100 parts by weight of the polythiopolymercaptan polymer, in combination with zinc oxide. As will be discussed in more detail in the following disclosure, the present invention describes the successful use of purified benzothiazyl disulfide in lower concentrations in combination with propionic acid activated, submicron zinc oxide.

BACKGROUND OF INVENTION

The present invention relates to a composition of matter suitable for use in converting a paste containing a polythiopolymercaptan polymer into a dental impression by human mouth placement for less than about ten minutes. The resulting elastomeric impression has the properties of low compression set, resistance to stress, dimensional stability and low toxicity suitable for making dental appliances by methods well known in the art.

An example of a liquid polythiopolymercaptan polymer which is transformed into a suitable elastomer by this invention is sold under the tradename Thiokol LP-2 and is manufactured by the Chemical Division of Thiokol Corporation. This polymer has the following properties:

Viscosity = 470 poises at 77° F.
Molecular weight = 400 (average)
Mercaptan content = 1.5–2.0 weight percent
Crosslinking = 2.0 mole percent due to 1,2,3-trichloropropane reaction Although the average structure of LP-2 is $HS(C_2H_4OCH_2OC_2H_4SS)_{23}C_2H_4OCH_2OC_2H_4SH$, indicating terminal thiol groups, pendant cross-linking thiols are also present to assist the development of elastomeric properties. This polymer is the essential component of the base paste of the normal two-paste system (base plus catalyst) for the purpose of admixing just prior to mouth placement.

The conventional catalyst used for curing LP-2 contains substantial lead peroxide which could be objectionable because of its toxicity and its dark-brown color which causes staining of skin and clothing and is especially difficult to remove.

The present invention is directed to a catalyst which comprises propionic acid treated, submicron zinc oxide and purified benzothiazyl disulfide (MBTS). The orally toxic dose (LD50) of MBTS for the rat is quite high 7 g/Kg), thus greatly exceeding the limiting dose (5 g/Kg) distinguishing human lethality, which is quite high.

The composition of the present invention also eliminates the objectionable color and stain associated with the prior art composition since the catalyst system comprises essentially light colored components. Therefore, the catalyst paste can be colored with any appropriate pigment (chemically inert and non-toxic) to provide for color contrast for indication of thorough mixing with the base paste.

An additional advantage of the present invention is the absence of significant shrinkage of the elastomeric impression since the cure system does not involve an oxidative condensation reaction of the thiols, to give water as a by-product. Metal peroxide curatives (lead peroxide, zinc peroxide, calcium peroxide) and cupric hydroxide give such condensation cures so that the resultant impression demonstrates significant negative dimensional change (shrinkage). Organic hydroperoxide cures also give significant shrinkage.

By comparison, the propionic acid treated zinc oxide-purified benzothiazyl disulfide system does not involve an oxidative attack on the thiol groups at the temperature of the mouth (less than 98.6° F.). Therefore, no volatile water by-product was formed, resulting in an elastomeric impression of considerable dimensional stability.

SUMMARY OF THE INVENTION

The present invention is directed to a catalyst paste composition having use in making elastomeric dental impressions. The catalyst paste composition comprises propionic acid treated, submicron zinc oxide which is accelerated with purified benzothiazyl disulfide (MBTS) at levels below 20 parts per hundred by weight of the light polythiopolymercaptan polymer (LP-2). Although a paste containing propionic acid activated zinc oxide will slowly cure the LP-2 containing base paste, the interaction with MBTS results in a catalyst system which provides rapid cure to an elastomer after mouth placement for less than about ten minutes. In some instances, this interaction may be promoted thermally by prior heat treating the catalyst paste before its mixing with the base paste.

Since MBTS alone will cause rubber reversion of cured LP-2, the presence of an excess of the zinc oxide in the catalyst composition is required (ZnO:MBTS weight ratio greater than about 2). In addition, the reversion of the elastomer to a less cured state is promoted by organic base impurities found in substantial amounts, 5–15%, in normal commercial grade MBTS. This is true because MBTS is manufactured by the oxidation of crude 2-mercaptobenzothiazole (MBT) prepared by the autoclave reaction of aniline, sulfur and carbon disulfide. This crude MBT contains a variety of impurities determined to be in substantial amounts—5–15% remaining in normal commercial grade MBTS. This crude MBT contains a variety of impurities such as benzothiazole, anilinobenzothiazole, 3-(2-benzothiazolyl)-2-benzothiazolinethione, phenyl isothiocyanate, diphenylthiourea, 2-aminothiophenol as well as unreacted aniline and sulfur (U.S. Pat. No. 3,904,638; Sagawa, Kunihiro, Kimura and Inoue, 1975). The organic impurities are believed to be deleterious in that they promote rubber reversion subsequent to the crosslinking, apparently by activation of MBTS. Therefore, as used in the present invention the MBTS requires purification by crystallization or efficient solvent extraction in order to essentially remove these accelerating-reversion inducing impurities. If these impurities are not sufficiently removed they reduce the working time of the mixed paste below the necessary 2–3 minutes during room temperature storage. Such MBTS containing catalysts require employment at lower concentration with the base and prior heat-treatment to achieve near stable activity (see Example IV).

The catalyst composition of the present invention involves the activation of the thiol group of LP-2 by coordination with zinc propionate coated submicron zinc oxide, which in combination with MBTS gives the rapid crosslinking reaction required for elastomeric cure. Using substantially pure MBTS lowers the required amount to less than 20 parts per hundred part of LP-2 by weight, thereby diminishing its rubber reversion influence. The excess propionic acid treated zinc oxide has the function of displacing the reaction towards crosslinking and inhibiting the reversion influence of MBTS. The catalyst paste heat activation requirement and its mix ratio with the base paste depends upon the MBTS purity.

DETAILED DESCRIPTION

The catalyst paste composition of this invention comprises zinc oxide curative, benzothiazyl disulfide (MBTS), inert plasticizer, inert pigment, inert flavorant and inert filler, if desirable. The concentration of the various ingredients is as follows in weight percent:

| | |
|---|---|
| organic acid treated zinc oxide | 40–60% |
| substantially pure benzothiazyl disulfide | 5–20% |
| plasticizer | 20–50% |
| coloring pigment | 0.1–2.5% |
| flavorant | 0.1–2.5% |
| filler | up to 35% |

The zinc oxide should be submicron, 90–100% less than one micron spherical diameter, and should be treated with propionic acid or other organic carboxylic acid to provide a zinc carboxylate coating. The propionic acid-treated zinc oxide of this invention contains zinc propionate and/or propionic acid equivalent to 0.2–0.7 weight percent of propionic acid. Depending upon the efficacy of the propionic acid treatment, the MBTS activity and the base:catalyst ratio, this zinc oxide can be employed in the catalyst paste to the extent of 20–100 parts by weight to 100 parts by weight of the polythiopolymercaptan polymer.

The MBTS purity is defined essentially by catalyst performance with respect to promotion of the elastomeric cure versus excessive acceleration-reversion. In terms of MBTS-MBT content it will normally contain a minimum MBTS purity of 92% and a maximum MBT content of 5% following extraction purification. Crystallization purification, of course, will increase this MBTS purity. The purified MBTS can be employed in the catalyst paste below 20 parts—normally 10–20 parts by 100 parts by weight of the polythiopolymercaptan liquid polymer.

As is to be expected with virtually any chemical production process, there are batch to batch variations among lots of benzothiazyl disulfide produced by a given source, as well as variations between sources. Not only are these variations seen in MBTS and MBT content, but also in as yet unidentified impurity content. Thus, even after extensive purification, either by solvent extraction or by recrystallization, two batches of benzothiazyl disulfide of very similar MBTS and MBT content can have quite disimilar catalytic activity in promoting the low temperature vulcanization of polythiopolymercaptan prepolymers by propionic acid treated zinc oxide.

This apparent dilemma is controllable in the present invention by "baby batch" testing of the reactivity of the various batches of benzothiazyl disulfide, followed by judicious formulation and blending, to obtain the desired degree of reactivity and suitable physical properties to adequately meet the requirements of the invention.

Suitable inert fillers which may be used with this catalyst are titanium dioxide and aluminum oxide. Phthalate esters, such as dibutyl phthalate, are suitably inert plasticizers. Other suitable plasticizer classes are diphenyl alkyl phosphate esters, polyalkylene glycol carboxylates and N-alkyl substituted toluene sulfonamides. The catalyst paste is also suitably colored with inert pigments, such as copper phthalocyanine blue or chlorinated copper phthalocyanine green, and contains appropriate flavorants such as 1-carvone or synthetic peppermint oil.

As previously stated above, some catalyst pastes are formulated to require heat-treatment activation. The base paste associated with the catalyst paste of this invention contains the polythiopolymercaptan liquid polymer containing crosslinking thiol groups, fillers and a plasticizer. As previously described, a suitable polymer is available under the trade name Thiokol LP-2, which has an average molecular weight of 4000, a viscosity of about 470 poises at 25° C. and a 2 mole percent of crosslinking functionality, based on reacted 1,2,3,-trichloropropane. Another suitable polymer is available under the tradename Thiokol LP-32, which contains 0.5 mole percent crosslinking functionality.

The catalyst paste of this invention and the base paste are mixed together in appropriate proportions to obtain a cured, elastomeric dental impression after mouth placement for less than about ten minutes. The resultant impression has suitable physical properties for processing the dental restorative prothesis. These properties include the special advantage of low shrinkage.

The following examples are illustrative of the properties obtained from catalyst paste compositions of this invention. In these examples, the zinc oxide and the benzothiazyl disulfide are those heretofore described in detail. Each solid component of the catalyst paste was blended by mixing with dibutyl phthalate. The catalyst paste was hand mixed for one minute in an equi-weight combination in case of Examples I and II, and in a ratio of 3:2 for Example III, and 3:1 for Example IV, with the base paste, which is sold under the tradename Permlastic, by Kerr Manufacturing Co., a Division of Sybron Corporation. The catalyst and base paste are mixed together by spatulation. The catalyst composition of the examples are based upon the previous designated combinations containing 100 parts by weight of LP-2. The working time is defined by the American Dental Association Specification No. 19 for elastomeric impression materials (effective Nov. 1, 1967, American National Standard Z156.19-1971). The compression set, strain in compression and dimensional stability are defined by the Revised American Dental Association Specification No. 19 (J. Am. Dental Assoc. 1977, 94 733-741).

EXAMPLE I

| Ingredients | Parts by Weight |
| --- | --- |
| LP-2 in base paste | 100.00 |
| Catalyst Paste: | |
| Zinc oxide | 82.38 |
| MBTS | 13.56 |
| Dibutyl phthalate | 39.15 |
| Titanium dioxide | 32.88 |
| Pigment (Copper phthalocyanine blue) | 1.53 |

Working time: 3-4 minutes
Six-minute cure at 32° C. gave the following physicals:
  Compression set: 1.4%
  Strain in Compression: 9.1%
Two weeks later, the room temperature rubber specimens were found to have strain in compression of 9.8%, demonstrating only slight reversion.

EXAMPLE II

| Ingredients | Parts by Weight |
| --- | --- |
| LP-2 in base paste | 100.00 |
| Catalyst paste: | |
| Zinc oxide | 67.80 |
| MBTS | 12.03 |
| Dibutyl phthalate | 44.75 |
| Titanium dioxide | 43.39 |
| Pigment | 1.53 |

Working time: 4-5 minutes
A 6-minute cure at 32° C. gave the following physicals:
  Compression set: 2.7%
  Strain in Compression: 11.3%
Two weeks later, the room temperature stored specimens were found to have strain in compression of 8.9%. The dimensional change after 24 hours at room temperature was −0.1 to −0.2%.

EXAMPLE III

| Ingredients | Parts by Weight |
| --- | --- |
| LP-2 in base paste | 100.00 |
| Catalyst paste: | |
| Zinc oxide | 47.16 |
| MBTS | 16.02 |
| Dibutyl phthalate | 24.92 |
| Pigment | 0.89 |

Working time: 7-8 minutes
A 6-minute cure at 32° C. gave the following physicals:
  Compression set: 1.3%
  Strain in Compression: 15.1%
Nine days later, this strain in compression has increased to 17.7%, demonstrating only slight reversion.

EXAMPLE IV

| Ingredients | Parts by Weight |
| --- | --- |
| LP-2 in base paste | 100.00 |
| Catalyst paste: | |
| Zinc oxide | 26.28 |
| MBTS | 10.66 |
| Dibutyl phthalate | 16.07 |
| Pigment | 0.50 |
| Flavorant | 2.01 |

The catalyst paste was given a 9-day heat-treatment at 60° C.
Working time: 6-7 minutes
An 8-minute cure at 32° C. gave the following physicals:
  Compression set: 2.3%
  Strain in Compression: 9.6%
Nine days later, this strain in compression was 8.3%.

The above examples are not intended to limit the scope of the invention or the applications to which this invention may be directed. It is to be understood that although the invention has been described with specific reference to particular embodiments thereof, it is not to be so limited, since changes and alterations therein may be made which are within the full intended scope of this invention as defined by the appended claims.

What is claimed is:

1. A catalyst composition in the form of a paste suitable for body temperature cure of liquid polythiopolymercaptan polymers which comprises in weight percent about 40 to 60 percent organic acid-treated, submicron zinc oxide, about 5 to 20 percent benzothiazyl disulfide having a purity of at least 92 percent by weight, and where the ratio of zinc oxide to benzothiazyl disulfide is at least about 2 to 1, and about 20 to 50 percent plasticizer.

2. The composition of claim 1 which further includes a coloring pigment in a concentration of about 0.1 to 2.5 percent and a flavorant in a concentration of about 0.1 to 2.5 percent.

3. The composition of claim 2 which further includes a filler in a concentration of up to about 35 percent.

4. The composition of claim 1 where the zinc oxide is submicron in particle diameter, with 90 percent being less than one micron diameter, and has been treated with propionic acid to contain about 0.2 to 0.7 percent as zinc propionate.

5. The composition of claim 2 where the benzothiazyl disulfide has a purity greater than 92 percent by weight.

* * * * *